United States Patent
Kim et al.

(10) Patent No.: US 11,865,141 B2
(45) Date of Patent: Jan. 9, 2024

(54) COMPOSITION FOR IMPROVING, PREVENTING OR TREATING SKIN DISEASE COMPRISING INDUCED PLURIPOTENCY STEM CELL-DERIVED MESENCHYMAL STEM CELLS PRETREATED WITH INTERFERON GAMMA AND EXOSOMES DERIVED THEREFROM

(71) Applicants: THE ASAN FOUNDATION, Seoul (KR); UNIVERSITY OF ULSAN FOUNDATION FOR INDUSTRY COOPERATION, Ulsan (KR)

(72) Inventors: Sue Kim, Seoul (KR); Jin Ho Yu, Seoul (KR)

(73) Assignees: THE ASAN FOUNDATION, Seoul (KR); UNIVERSITY OF ULSAN FOUNDATION FOR INDUSTRY COOPERATION, Gyeongsangnam-do (KR)

( * ) Notice: Subject to any disclaimer, the term of this patent is extended or adjusted under 35 U.S.C. 154(b) by 481 days.

(21) Appl. No.: 16/959,366

(22) PCT Filed: Jan. 7, 2019

(86) PCT No.: PCT/KR2019/000181
§ 371 (c)(1),
(2) Date: Jun. 30, 2020

(87) PCT Pub. No.: WO2019/135645
PCT Pub. Date: Jul. 11, 2019

(65) Prior Publication Data
US 2021/0060081 A1    Mar. 4, 2021

(30) Foreign Application Priority Data
Jan. 5, 2018 (KR) .......... 10-2018-0001979

(51) Int. Cl.
A61K 35/28 (2015.01)
A61P 17/00 (2006.01)
C12N 5/077 (2010.01)

(52) U.S. Cl.
CPC .............. *A61K 35/28* (2013.01); *A61P 17/00* (2018.01); *C12N 5/0652* (2013.01)

(58) Field of Classification Search
CPC ....... A61K 35/28; A61P 17/00; C12N 5/0652; C12N 2501/24; C12N 2506/45
See application file for complete search history.

(56) References Cited

U.S. PATENT DOCUMENTS

| | | | |
|---|---|---|---|
| 2011/0003008 A1 | 1/2011 | Lim | |
| 2015/0203820 A1* | 7/2015 | Wang | C12N 5/0662 |
| | | | 435/366 |

FOREIGN PATENT DOCUMENTS

| | | |
|---|---|---|
| CN | 102014934 A | 4/2011 |
| CN | 107245472 A | 10/2017 |
| CN | 110072534 A | 7/2019 |
| KR | 10-2013-0073794 A | 7/2013 |
| KR | 10-2015-0004822 A | 1/2015 |
| KR | 10-2016-0037113 A | 4/2016 |
| WO | 2009-105044 A1 | 8/2009 |
| WO | WO-2016/048107 A1 | 3/2016 |
| WO | WO-2016048107 A1 * | 3/2016 ............. A61K 35/12 |
| WO | WO-2017/204639 A1 | 11/2017 |
| WO | WO-2018/071677 A1 | 4/2018 |

OTHER PUBLICATIONS

EESR of EP Application No. EP19735826.0 dated Mar. 5, 2021.
Zhang, Q., et al.; "Exosomes originating from MSCs stimulated with TGF-β and IFN-γ promote Treg differentiation", J. Cell Physiol., 2018, 233, 6832-6840.
Yu, et al. (2014) "Exosomes Derived from Mesenchymal Stem Cells." Int. J. Mol. Sci., 15:4142-4157; doi:10.3390/ijms15034142.
International Search Report, dated May 27, 2019, issued in corresponding International Patent Application No. PCT/KR2019/000181, with English Translation.
Office Action of European Patent Application No. 19735826.0 dated Jan. 27, 2023.
Office Action of Chinese Patent Application No. 201980007408.2 dated Mar. 8, 2023.

* cited by examiner

*Primary Examiner* — Taeyoon Kim
(74) *Attorney, Agent, or Firm* — Harness, Dickey & Pierce, P.L.C.

(57) ABSTRACT

The present invention may provide a method for producing induced pluripotency stem cell-derived mesenchymal stem cells (IFNγ-iMSC) pretreated with interferon-gamma; induced pluripotency stem cell-derived mesenchymal stem cells pretreated with interferon-gamma prepared by the method; a pharmaceutical composition for preventing or treating skin diseases, and a cosmetic composition for preventing or improving skin diseases, comprising culture thereof or exosome (IFNγ-iMSC-exo) isolated therefrom as an active ingredient. When the composition of the present invention is used, it is possible to provide a composition for skin diseases and a stem cell therapeutic agent, which have an improved immunomodulating function over conventional mesenchymal stem cells.

2 Claims, 9 Drawing Sheets

Specification includes a Sequence Listing.

INFγ-MSC-Exo

INFγ-iMSC-Exo

COMPOSITION FOR IMPROVING, PREVENTING OR TREATING SKIN DISEASE COMPRISING INDUCED PLURIPOTENCY STEM CELL-DERIVED MESENCHYMAL STEM CELLS PRETREATED WITH INTERFERON GAMMA AND EXOSOMES DERIVED THEREFROM

CROSS-REFERENCE TO RELATED APPLICATIONS

This application is a national phase application of PCT Application No. PCT/KR2019/000181, filed on Jan. 7, 2019, which claims the benefit and priority to Korean Patent Application No. 10-2018-0001979, filed on Jan. 5, 2018. The entire disclosures of the applications identified in this paragraph are incorporated herein by references.

FIELD

The present invention was made by Project No. NRF-2015K1A4A3046807 under the support of the Ministry of Science and ICT in Korea and the project was carried out in the project named "Asan-Minnesota Institute for Innovating Transplantation" within the program titled "Leading Foreign Research Institute Recruitment Program" by "Asan Medical Center" under management of the National Research Foundation of Korea, from 1 Sep. 2015 to 31 Aug. 2021.

The present invention relates to a composition for alleviation, prevention, or treatment of a skin disease, the composition comprising interferon-gamma-pretreated induced pluripotent stem cell-derived mesenchymal stem cells (IFNγ-iMSCs), a culture thereof, and/or exosomes derived from IFNγ-iMSCs or a culture of IFNγ-iMSCs.

BACKGROUND

Atopic dermatitis (AD), also known as atopic eczema, is a very common inflammatory skin disease, and is known to affect approximately 5-20% of children worldwide. The pathogenesis of acute AD has been reported to be associated with Th2 inflammatory responses mediated by the dermal infiltration of CD4+ T cells and eosinophils and the increased release of immunoglobulin E (IgE) and Th2 cytokine. There is no known direct specific therapy for AD so far, and the development of novel therapies for AD is urgent.

Mesenchymal stem cells, which are highly proliferative adherent cells having multipotency to differentiate into bone, cartilage, fat, and the like, have been known to have anti-inflammatory and immunomodulatory capabilities. Mesenchymal stem cells exhibit immunosuppressive effects, for example, suppressing proliferation and differentiation of T cells and B cells and suppressing functions of immune cells, such as dendritic cells, natural killer (NK) cells, and macrophages. A study was recently reported that mesenchymal stem cells were transplanted together with hematopoietic stem cells to increase engraftment of the hematopoietic stem cells. It has been also reported that mesenchymal stem cells reduce inflammation and inhibit autoimmune hyperreactivity in diseases, such as graft-versus-host disease (GVHD), collagen-induced arthritis (CIA), experimental autoimmune encephalomyelitis (EAE), systemic lupus erythematosus (SLE), sepsis, acute pancreatitis (AP), colitis, multiple sclerosis (MS), and rheumatoid arthritis.

Exosomes are lipid-bilayer vesicles and correspond to a component of extracellularly secreted substances. Exosomes are known to transport intracellular biomolecules, such as proteins, bioactive lipids, and RNA (miRNA), so as to perform a functional role of mediating cell-cell communication and cellular immunity. These exosomes are also being studied as a biomarker for a neurological disease, such as Alzheimer's disease, and also utilized in the development of drug delivery systems, such as nanocarriers of specific drugs, due to highly selective penetration thereof to penetrate into the blood-brain barrier (BBB) that separates cerebrospinal fluid and blood.

Exosomes secreted from mesenchymal stem cells are known to be involved in cell-to-cell communication and show therapeutic efficacy of stem cells in regenerative medicine. In recent years, studies about therapeutic effects on various types of disease by using exosomes secreted from mesenchymal stem cells instead of mesenchymal stem cells per se are being actively conducted.

The present inventors have conducted intensive and thorough research into the development of therapeutic agents for atopic dermatitis using mesenchymal stem cells and exosomes thereof. As a result, the present inventors have established that IFN-γ-pretreated induced pluripotent stem cell (iPSC)-derived mesenchymal stem cells (MSCs) [IFNγ-iMSCs] have an improved anti-inflammatory activity compared with existing mesenchymal stem cells, and the IFN-γ-pretreated induced pluripotent stem cell-derived mesenchymal stem cells and exosomes therefrom (IFNγ-iMSC-exo) show skin disease alleviation effects, and then have completed the present invention.

SUMMARY

Technical Problem

An aspect of the present invention is to provide a method for producing interferon-gamma-pretreated induced pluripotent stem cell-derived mesenchymal stem cells (IFNγ-iMSCs).

Another aspect of the present invention is to provide interferon-gamma-pretreated induced pluripotent stem cell (iPSC)-derived mesenchymal stem cells (MSCs) [IFNγ-iMSCs).

Still another aspect of the present invention is to provide a pharmaceutical composition for prevention or treatment of a skin disease, the composition comprising interferon-gamma-pretreated induced pluripotent stem cell (iPSC)-derived mesenchymal stem cells (MSCs) [IFNγ-iMSCs) and/or exosomes isolated therefrom (IFNγ-iMSC-derived exosomes or IFNγ-iMSC-exo).

Another aspect of the present invention is to provide a cosmetic composition for prevention or alleviation of a skin disease, the composition comprising interferon-gamma-pretreated induced pluripotent stem cell-derived mesenchymal stem cells (IFNγ-iMSCs) and/or exosomes isolated therefrom (IFNγ-iMSC-exo).

Still another aspect of the present invention is to provide exosomes isolated from interferon-gamma-pretreated induced pluripotent stem cell-derived mesenchymal stem cells (IFNγ-iMSCs) or a culture thereof (IFNγ-iMSC-exo).

Another aspect of the present invention is to provide a method for producing exosomes isolated from interferon-gamma-pretreated induced pluripotent stem cell-derived mesenchymal stem cells (IFNγ-iMSCs).

Still another aspect of the present invention is to provide a stem cell therapeutic agent comprising IFNγ-iMSCs and/or IFNγ-iMSC-exo.

Technical Solution

In accordance with an aspect of the present invention, there is provided a method for producing interferon-gamma-pretreated induced pluripotent stem cell-derived mesenchymal stem cells (IFNγ-iMSCs), the method comprising: culturing induced pluripotent stem cell-derived mesenchymal stem cells (iMSCs) in a cell culture medium containing interferon-gamma.

The present inventors have conducted intensive and thorough research into the development of therapeutic agents for atopic dermatitis using mesenchymal stem cells and exosomes thereof. As a result, the present inventors have established that IFN-γ-pretreated induced pluripotent stem cell (iPSC)-derived mesenchymal stem cells (MSCs) [IFNγ-iMSCs] have an improved anti-inflammatory activity compared with existing mesenchymal stem cells, and the IFN-γ-pretreated induced pluripotent stem cell-derived mesenchymal stem cells and exosomes therefrom (IFNγ-iMSC-exo) show skin disease alleviation effects.

As used herein, the term "induced pluripotent stem cell (iPSC)" refers to a cell having pluripotency, obtained by inducing dedifferentiation of an already differentiated cell, such as a somatic cell, to return to an initial undifferentiated state. The dedifferentiation can be induced by introducing and expressing a particular gene (for example, Sox2, c-Myc, Klf4, Oct-4, or the like) or injecting a dedifferentiation-inducing protein produced from cells into which the particular gene is introduced. The pluripotency means the ability to differentiate into tissues or organs originating from three germ layers constituting the living body, that is, endoderm, mesoderm, and ectoderm.

The induced pluripotent stem cells of the present invention encompass induced pluripotent stem cells derived from all mammals, such as humans, monkeys, pigs, horses, cows, sheep, dogs, cats, rats, and rabbits, but are preferably induced pluripotent stem cells derived from humans.

As used herein, the term "mesenchymal stem cells" refers to multipotent stem cells to be able to differentiate into cells of fat, cartilage, bone, muscle, skin, nerve, and the like. The mesenchymal stem cells may be differentiated from induced pluripotent stem cells, or may be isolated from bone marrow, adipose tissue, umbilical cord tissue, umbilical cord blood, skeletal muscle, peripheral blood, synovial, amniotic fluid, or the like.

As used herein, the term "induced pluripotent stem cell-derived mesenchymal stem cells" refers to mesenchymal stem cells differentiated from induced pluripotent stem cells (iMSCs).

In an embodiment of the present invention, the induced pluripotent stem cell-derived mesenchymal stem cells are characterized by (i) an increase in expression of indoleamine 2,3-dioxygenase and (ii) a reduction in secretion of an inflammatory cytokine, when compared with mesenchymal stem cells isolated from the interior of the body (for example, bone marrow, adipose tissue, umbilical cord tissue, umbilical cord blood, skeletal muscle, peripheral blood, synovial, amniotic fluid, or the like).

The inflammatory cytokine is at least one inflammatory cytokine selected from the group consisting of IL-19, IL-22, IL-1β, IL-6, and IL-6R α.

As used herein, the term "exosome" refers to a membrane vesicle that is extracellularly secreted from a cell or has a membrane structure composed of a lipid-bilayer present in the cell, and the exosome exists in the body fluid of almost all eukaryotes. Exosomes have a diameter of approximately 30-100 nm, and exosomes are released from cells when multivesicular bodies are fused to cell membranes, or released directly from cell membranes. Exosomes are well known to serve to transport intracellular biomolecules, such as proteins, bioactive lipids, and RNA (miRNA), so as to perform a functional role of mediating coagulation, cell-cell communication, and cellular immunity. In the present invention, the concept of the exosomes encompasses microvesicles. The marker proteins of exosomes are known to be CD63, CD81, or the like, and besides, are known to be proteins, for example, cell surface receptors such as EGFR, signaling-related molecules, cell adhesion-related proteins, MSC-associated antigens, heat shock proteins, vesiculation-related Alix.

In an embodiment of the present invention, the induced pluripotent stem cell-derived mesenchymal stem cells are mesenchymal stem cells obtained by culturing induced pluripotent stem cells in an extracellular matrix-coated culture vessel, followed by differentiation.

As used herein, the term "extracellular matrix" refers to a physical environment in which biochemical factors required for cells to grow and differentiate are stored, appropriately supplied, and can be recognized by cells.

In an embodiment of the present invention, the extracellular matrix is an extracellular matrix protein.

In another embodiment of the present invention, examples of the extracellular protein include vitronectin, fibronectin, laminin, elastin, collagen, and the like, but are not limited thereto.

In a specific embodiment of the present invention, the extracellular protein is vitronectin.

The method for producing interferon-gamma-pretreated induced pluripotent stem cell-derived mesenchymal stem cells of the present invention comprises culturing induced pluripotent stem cell-derived mesenchymal stem cells in a cell culture medium containing interferon-gamma.

The interferon-gamma (interferon-γ, IFN-γ, or IFNγ) used to pretreat the induced pluripotent stem cell-derived mesenchymal stem cells of the present invention is a cytokine that is produced by activated T cells, NK cells, and CD4- and CD8-positive lymphocytes. The interferon-gamma, which is a differentiation-promoting factor or growth factor, is involved in actions of increasing the activation, proliferation, and differentiation of various cells including T lymphocytes and the MHC expression of antigen-presenting cells and plays an important role in immune and inflammatory responses.

As used herein, the term "pretreatment" refers to a procedure in which an interferon-gamma-added cell culture medium is contacted with induced pluripotent stem cell-derived mesenchymal stem cells in the procedure of culturing induced pluripotent stem cell-derived mesenchymal stem cells.

The cell culture medium for producing the interferon-gamma-pretreated induced pluripotent stem cell-derived mesenchymal stem cells of the present invention may be any medium that is usually used in animal cell culture, for example, Dulbecco's modification of Eagle's medium (DMEM), a mixture of DMEM and F12, Eagle's minimum essential medium (Eagle's MEM), α-MEM, Iscove's MEM, 199 medium, CMRL 1066, RPMI 1640, F12, F10, Waymouth's MB752/1, McCoy's 5A, MCDB series, and the like may be used.

In an embodiment of the present invention, the interferon-gamma is contained in the cell culture medium at a concentration of 1-100 ng/ml.

In another embodiment of the present invention, the interferon-gamma is contained in the cell culture medium at a concentration of 1-90 ng/ml, 1-80 ng/ml, 1-70 ng/ml, 1-60 ng/ml, 1-50 ng/ml, 1-40 ng/ml, 1-30 ng/ml, 10-90 ng/ml, 10-80 ng/ml, 10-70 ng/ml, 10-60 ng/ml, 10-50 ng/ml, 10-40 ng/ml, and 10-30 ng/ml.

In an embodiment of the present invention, the culturing is performed for 6-48 hours.

In another embodiment of the present invention, the culturing is performed for 6-42 hours, 6-36 hours, 6-30 hours, 6-27 hours, 12-48 hours, 12-42 hours, 12-36 hours, 12-30 hours, 12-27 hours, 18-48 hours, 18-42 hours, 18-36 hours, 18-30 hours, 18-27 hours, 21-48 hours, 21-42 hours, 21-36 hours, 21-30 hours, or 21-27 hours.

In accordance with another aspect of the present invention, there are provided interferon-gamma-pretreated induced stem cell-derived mesenchymal stem cells (IFNγ-iMSCs).

In an embodiment of the present invention, the mesenchymal stem cells are produced by the method for producing interferon-gamma-pretreated induced stem cell-derived mesenchymal stem cells.

In accordance still another of the present invention, there is provided a pharmaceutical composition for prevention or treatment of a skin disease, the composition comprising interferon-gamma-pretreated induced pluripotent stem cell-derived mesenchymal stem cells or a culture thereof as an active ingredient.

As used herein, the term "culture" refers to a culture liquid obtained by culturing interferon-gamma-pretreated induced pluripotent stem cell-derived mesenchymal stem cells in a culture medium, or a dried, diluted, filtered, and/or concentrated product of the culture liquid. The culture may contain or not contain the induced pluripotent stem cell-derived mesenchymal stem cells.

As used herein, the term "comprising as active ingredient" refers to comprising the interferon-gamma-pretreated induced pluripotent stem cell-derived mesenchymal stem cells, the culture thereof, or the exosomes isolated therefrom, of the present invention, in an amount sufficient to attain activity to alleviate, prevent, or treat a skin disease.

As used herein, the term "skin disease" refers to an abnormal condition or symptom occurring in the skin.

In an embodiment of the present invention, the skin disease is an inflammatory skin disease. The inflammatory skin disease means a skin disease that causes symptoms, such as itching and erythema, due to immune cell-mediated inflammatory responses.

In another embodiment of the present invention, the inflammatory skin disease is a skin disease selected from the group consisting of atopic dermatitis, contact dermatitis, and psoriasis.

As used herein, the term "atopic dermatitis" refers to a skin eczema disease that is accompanied by chronically relapsing severe itching, and the atopic dermatitis is a type of dermatitis.

As used herein, the term "prevention" refers to all acts of suppressing a skin disease or disorder or delaying the progress of a skin disease or disorder by the administration of the composition of the present invention.

As used herein, the term "treatment" refers to (a) suppressing the development of a skin disease or disorder; (b) alleviating a skin disease or disorder; and (c) removing a skin disease or disorder.

The composition of the present invention may be prepared into a pharmaceutical composition.

According to a preferable embodiment of the present invention, the composition of the present invention is a pharmaceutical composition comprising: (a) a pharmaceutically effective amount of the above-described interferon-gamma-pretreated induced pluripotent stem cell-derived mesenchymal stem cells or culture thereof of the present invention; and (b) a pharmaceutically acceptable carrier. As used herein, the term "pharmaceutically effective amount" refers to an amount sufficient to attain efficacy or activity of the above-described induced pluripotent stem cell-derived mesenchymal stem cells or culture thereof.

In cases where the composition of the present invention is prepared into a pharmaceutical composition, the pharmaceutical composition of the present invention comprises a pharmaceutically acceptable carrier. The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like. The pharmaceutical composition of the present invention may further comprise, in addition to the above ingredients, a lubricant, a humectant, a sweetener, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present invention may be administered orally or parenterally, and for example, intravenous administration, subcutaneous administration, intramuscular administration, intraperitoneal administration, topical administration, intranasal administration, intrapulmonary administration, rectal administration, intrathecal administration, ocular administration, percutaneous administration, and transdermal administration may be employed.

A suitable dose of the pharmaceutical composition of the present invention may be variously prescribed depending on various factors, such as the method of formulation, the manner of administration, patient's age, body weight, gender, or morbidity, food, time of administration, route of administration, excretion rate, and response sensitivity. A general dose of the pharmaceutical composition of the present invention is within a range of 0.0001-1000 mg/kg in adults, but is not limited thereto.

In an embodiment of the present invention, the dose of the pharmaceutical composition of the present invention may be 0.001-1000 mg/kg, 0.01-1000 mg/kg, 0.1-1000 mg/kg, 1-1000 mg/kg, 5-1000 mg/kg, 10-1000 mg/kg, 20-1000 mg/kg, 30-1000 mg/kg, 50-1000 mg/kg, 100-1000 mg/kg, 0.0001-100 mg/kg, 0.001-100 mg/kg, 0.01-100 mg/kg, 0.1-100 mg/kg, 1-100 mg/kg, 5-100 mg/kg, 10-100 mg/kg, 20-100 mg/kg, 30-100 mg/kg, or 50-100 mg/kg, more specifically, 1, 5, 10, 15, 20, 25, 30, 35, 40, 45, 50, 55, 60, 65, 70, 75, 80, 85, 90, 95, 100, 150, 200, 250, 300, 350, 400, 450, 500, 750, or 1000 mg/kg.

The pharmaceutical composition of the present invention may be formulated using a pharmaceutically acceptable carrier and/or excipient according to a method that could be easily performed by a person having ordinary skills in the art to which the present invention pertains, and the composition of the present invention may be prepared into a unit dosage form or may be contained in a multi-dose container. Here, the formulation may be in the form of a solution in an oily or aqueous medium, a suspension, a syrup, an emulsion, an extract, a pulvis, a powder, granules, a tablet, or a capsule, and may further comprise a dispersant or a stabilizer.

In accordance with another aspect of the present invention, there is provided a cosmetic composition for prevention or alleviation of a skin disease, the composition comprising interferon-gamma-pretreated induced pluripotent stem cell-derived mesenchymal stem cells or a culture thereof as an active ingredient.

Since the cosmetic composition for prevention or alleviation of a skin disease according to the present invention has the same active ingredient and target disease as the above-described pharmaceutical composition for prevention or treatment of a skin disease, a description of overlapping contents therebetween is omitted to avoid excessive complexity of the present specification.

As used herein, the term "alleviation" refers to all acts of improving or beneficially changing symptoms of a disease by administration of the composition of the present invention.

The composition of the present invention may be prepared into a cosmetic composition. When the composition comprising the interferon-gamma-pretreated induced pluripotent stem cell-derived mesenchymal stem cells or culture thereof as an active ingredient for prevention or alleviation of a skin disease according to the present invention is prepared into a cosmetic composition, the cosmetic composition comprises, in addition to the interferon-gamma-pretreated induced pluripotent stem cell-derived mesenchymal stem cells or culture thereof as an active ingredient, ingredients that are usually used in a cosmetic composition, for example, a carrier, and common adjuvants, such as a stabilizer, a solubilizer, a vitamin, a pigment, and a flavoring.

The cosmetic composition of the present invention may be prepared into any formulation that is usually prepared in the art, and examples thereof may include a solution, a suspension, an emulsion, a paste, a gel, a cream, a lotion, a powder, a soap, a surfactant-containing cleanser, an oil, a powder foundation, an emulsion foundation, a wax foundation, and a spray, but are not limited thereto. More specifically, the cosmetic composition of the present invention may be prepared in a dosage form of emollient lotion, nourishing lotion, nourishing cream, massage cream, essence, eye cream, cleansing cream, cleansing foam, cleansing water, pack, spray, or powder.

In cases where the formulation of the present invention is a paste, a cream, or a gel, examples of a carrier component thereof may include animal fibers, vegetable fibers, wax, paraffin, starch, tragacanth, cellulose derivatives, polyethylene glycol, silicone, bentonite, silica, talc, and zinc oxide.

In cases where the formulation of the present invention is a powder or a spray, examples of a carrier component thereof may include lactose, talc, silica, aluminum hydroxide, calcium silicate, or a polyamide powder. Especially, in cases where the formulation of the present invention is a spray, the spray may further comprise a propellant, such as chlorofluorohydrocarbon, propane/butane, or dimethyl ether.

In cases where the formulation of the present invention is a solution or an emulsion, examples of a carrier component thereof may include a solvent, a solubilizer, or an emulsifier, and for example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan.

In cases where the formulation of the present invention is a suspension, examples of a carrier component thereof may include: a liquid-phase diluent, such as water, ethanol, or propylene glycol; a suspending agent, such as ethoxylated isostearyl alcohol, polyoxyethylene sorbitol ester, or polyoxyethylene sorbitan ester; microcrystalline cellulose; aluminum metahydroxide; bentonite, agar; or tragacanth.

In cases where the formulation of the present invention is a surfactant-containing cleanser, examples of a carrier component thereof may include aliphatic alcohol sulfate, aliphatic alcohol ether sulfate, sulfosuccinic acid monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, or ethoxylated glycerol fatty acid ester.

In accordance with still another aspect of the present invention, there are provided exosomes isolated from the interferon-gamma-pretreated induced pluripotent stem cell-derived mesenchymal stem cells or culture thereof of the present invention.

The interferon-gamma-pretreated induced pluripotent stem cell-derived mesenchymal stem cells (IFNγ-iMSCs) of the present invention are mesenchymal stem cells that have cytological (immunological) features distinguished from those of conventional mesenchymal stem cells (MSCs) or induced pluripotent stem cell-derived mesenchymal stem cells (iMSCs) without interferon-gamma treatment. As validated in an example of the present invention, the expression level of indoleamine 2,3-dioxygenase (IDO) was compared among the interferon-gamma-pretreated induced pluripotent stem cell-derived mesenchymal stem cells (IFNγ-iMSCs) of the present invention, general mesenchymal stem cells (MSCs), and the induced pluripotent stem cell-derived mesenchymal stem cells (iMSCs), and as a result, IDO was more highly expressed in iMSCs (not shown) rather than MSCs, and in IFNγ-iMSCs rather than iMSCs (FIG. 3). In addition, the cultures of iMSCs and IFNγ-iMSCs were separately collected to compare the levels of secretion of inflammation-related cytokine proteins therebetween, and as a result, it was verified that compared with iMSCs, the IFNγ-iMSCs of the present invention showed significantly reduced secretion of IL-19, IL-20, IL-1β, IL-6, and IL-6Rα (FIG. 4).

According to another aspect of the present invention, there is provided a pharmaceutical composition for prevention or treatment of a skin disease, the composition comprising, as an active ingredient, exosomes isolated from interferon-gamma-pretreated induced pluripotent stem cell-derived mesenchymal stem cells or a culture thereof.

According to still another aspect of the present invention, there is provided a cosmetic composition for prevention or alleviation of a skin disease, the composition comprising, as an active ingredient, exosomes isolated from interferon-gamma-pretreated induced pluripotent stem cell-derived mesenchymal stem cells or a culture thereof.

Since the pharmaceutical composition for prevention or treatment of a skin disease and the cosmetic composition for prevention or alleviation of a skin disease according to the present invention, each of which comprises as an active ingredient exosomes isolated from interferon-gamma-pretreated induced pluripotent stem cell-derived mesenchymal stem cells or a culture thereof, comprise as an active ingredient the above-described exosomes isolated from interferon-gamma-pretreated induced pluripotent stem cell-derived mesenchymal stem cells or a culture thereof and have the same target disease as the above-described pharmaceutical composition, a description of overlapping contents therebetween is omitted to avoid excessive complexity of the present specification.

In accordance with an aspect of the present invention, there is provided a method for treating a skin disease in a subject in need thereof, the method comprising administering to the subject a composition comprising as an active ingredient interferon-gamma-pretreated induced pluripotent stem cell-derived mesenchymal stem cells or a culture thereof, or exosomes isolated from interferon-gamma-pretreated induced pluripotent stem cell-derived mesenchymal stem cells or a culture thereof.

In accordance with another aspect of the present invention, there is provided a method for alleviating a skin disease in a subject in need thereof, the method comprising administering to the subject a composition comprising as an active ingredient interferon-gamma-pretreated induced pluripotent stem cell-derived mesenchymal stem cells or a culture thereof, or exosomes isolated from interferon-gamma-pretreated induced pluripotent stem cell-derived mesenchymal stem cells or a culture thereof.

The skin disease, which is a target disease of the treatment method or alleviation method of the present invention, is as defined with respect to the target disease of the pharmaceutical composition.

In an embodiment of the present invention, the subject is a mammal or a human.

Since the method for treating or alleviating a skin disease according to the present invention uses the same active ingredient as the above-described composition comprising, as an active ingredient, interferon-gamma-pretreated induced pluripotent stem cell-derived mesenchymal stem cells or a culture thereof, or exosomes isolated from interferon-gamma-pretreated induced pluripotent stem cell-derived mesenchymal stem cells or a culture thereof, a description of overlapping contents therebetween is omitted to avoid excessive complexity of the present specification.

In accordance with another aspect of the present invention, there is provided a method for producing exosomes isolated from interferon-gamma-pretreated induced pluripotent stem cell-derived mesenchymal stem cells (IFNγ-iMSCs), the method comprising:
  (a) culturing induced pluripotent stem cell-derived mesenchymal stem cells in a cell culture medium containing interferon-gamma;
  (b) washing the cultured mesenchymal stem cells, followed by additional culture in a cell culture medium; and
  (c) isolating exosomes from a culture of the mesenchymal stem cells.

Since the method for producing exosomes isolated from interferon-gamma-pretreated induced pluripotent stem cell-derived mesenchymal stem cells according to the present invention is a method for producing exosomes from the above-described interferon-gamma-pretreated induced pluripotent stem cell-derived mesenchymal stem cells produced by the method for producing interferon-gamma-pretreated induced pluripotent stem cell-derived mesenchymal stem cells, a description of overlapping contents therebetween is omitted to avoid excessive complexity of the present specification.

In an embodiment of the present invention, in step (c), the exosomes may be isolated from the culture of mesenchymal stem cells through centrifugation.

More specifically, the culture of mesenchymal stem cells is subjected to centrifugation at 200-400×g for 5-20 minutes to remove remaining cells and cell debris; the supernatant is collected and subjected to high-speed centrifugation at 9,000-12,000×g for 60-80 minutes; and then the supernatant is again collected and subjected to ultracentrifugation at 90,000-120,000×g for 80-100 minutes to remove a supernatant, and thus exosomes remaining in the bottom layer can be obtained. According to a specific embodiment of the present invention, the culture of mesenchymal stem cells is collected, centrifuged at 300×g for 10 minutes to remove remaining cells and cell debris, and then the supernatant is collected, filtered using a 0.22-μm filter, and then centrifuged at 10,000×g and 4° C. for 70 minutes using a high-speed centrifuge. The centrifuged supernatant is again collected, and centrifuged at 100,000×g and 4° C. for 90 minutes using an ultracentrifuge to remove a supernatant, and thus exosomes remaining in the bottom layer were isolated.

In accordance with still another aspect of the present invention, there is provided a stem cell therapeutic agent comprising, as an active ingredient, interferon-gamma-pretreated induced pluripotent stem cell-derived mesenchymal stem cells (IFNγ-iMSCs) or exosomes isolated therefrom (IFNγ-iMSC-exo).

As used herein, the term "stem cell therapeutic agent" refers to a pharmaceutical composition comprising stem cells as an active ingredient, and the stem cell therapeutic agent is used for the purpose of tissue regeneration, organ function recovery, or immune cell function control.

In an embodiment of the present invention, the stem cell therapeutic agent is a pharmaceutical composition of prevention or treatment of a disease from which recovery is expected through pluripotency of mesenchymal stem cells (for example, a disease associated with the heart, liver, joint, nervous systems, or immunity).

The stem cell therapeutic agent has a common component with the above-described pharmaceutical composition and cosmetic composition of the present invention, each of the compositions comprising interferon-gamma-pretreated induced pluripotent stem cell-derived mesenchymal stem cells or a culture thereof, or exosomes isolated therefrom, a description of overlapping contents therebetween is omitted to avoid excessive complexity of the present specification.

Advantageous Effects

Features and advantages of the present invention are summarized as follows.

(a) The present invention provides: a method for producing interferon-gamma-pretreated induced pluripotent stem cell-derived mesenchymal stem cells (IFNγ-iMSCs); interferon-gamma-pretreated induced pluripotent stem cell-derived mesenchymal stem cells produced by the method; and a pharmaceutical composition for prevention or treatment of a skin disease and a cosmetic composition for prevention or alleviation of a skin disease, each of the compositions comprising as an active ingredient the interferon-gamma-pretreated induced pluripotent stem cell-derived mesenchymal stem cells.

(b) The present invention provides a pharmaceutical composition for prevention or treatment of a skin disease and a cosmetic composition for prevention or alleviation of a skin disease, each of the compositions comprising as an active ingredient exosomes isolated from interferon-gamma-pretreated induced pluripotent stem cell-derived mesenchymal stem cells or a culture thereof (IFNγ-iMSC-exo).

(c) The use of the compositions of the present invention can provide compositions for a skin disease and a stem cell therapeutic agent, each having an immunomodulatory function further improved compared with existing mesenchymal stem cells.

DETAILED DESCRIPTION

Hereinafter, the present invention will be described in more detail with reference to e xamples. These examples are only for illustrating the present invention more specifically, and it would be apparent to those skilled in the art that the scope of the present invention is not limited by these examples according to the gist of the present invention.

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

EXAMPLE 1

Figure 1:
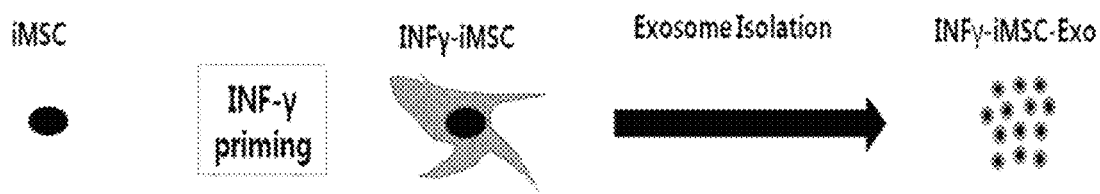
FIG. 1 schematically shows the manufacture of interferon-gamma-pretreated induced pluripotent stem cell-derived mesenchymal stem cells (IFNγ-iMSCs) and exosomes derived from the mesenchymal stem cells (IFNγ-iMSC-exo).

Manufacture and Assay of Induced Pluripotent Stem Cell-Derived Mesenchymal Stem Cells Induced pluripotent stem cells (induced pluripotent stem cell (fibroblasts, peripheral blood mononuclear cells (PBMCs), or mesenchymal stem cells (MSCs)-originated induced pluripotent stem cell (iPSC) lines established by the Stem Cell Center of Asan Medical Center), which were cultured in DMEM/F-12 supplemented with Knockout xeno-free serum replacement, glutamax, non-essential amino acids, beta-mercaptoethanol, antibiotic, and basic fibroblast growth factor (bFGF) without the use of feeder cells, were plated onto culture dishes previously coated with vitronectin, and then the differentiation of mesenchymal stem cells was induced at 37° C. using DMEM supplemented with 10% FBS (v/v), 5 ng/ml basic FGF, 0.1 mM minimum essential media non-essential amino acids (MEM NEAA), β-mercaptoethanol (1×), 100 unit/ml penicillin, and 100 μg/ml streptomycin. On day 7 of culture, the cells were dissociated into single cells by incubation in TrypLE express (1×), transferred onto cell culture plates, and then further incubated for 7 days. While media were exchanged every two days, the differentiation into mesenchymal stem cells (iMSCs) with a flat and elongated appearance was observed. On the completion of the induction of differentiation into mesenchymal stem cells for 14 days, the cells were treated with 20 ng/ml interferon-y (IFN-γ) for 24 hours. After 24 hours, the cells were washed with PBS, followed by additional incubation (FIG. 1).

Figure 2:
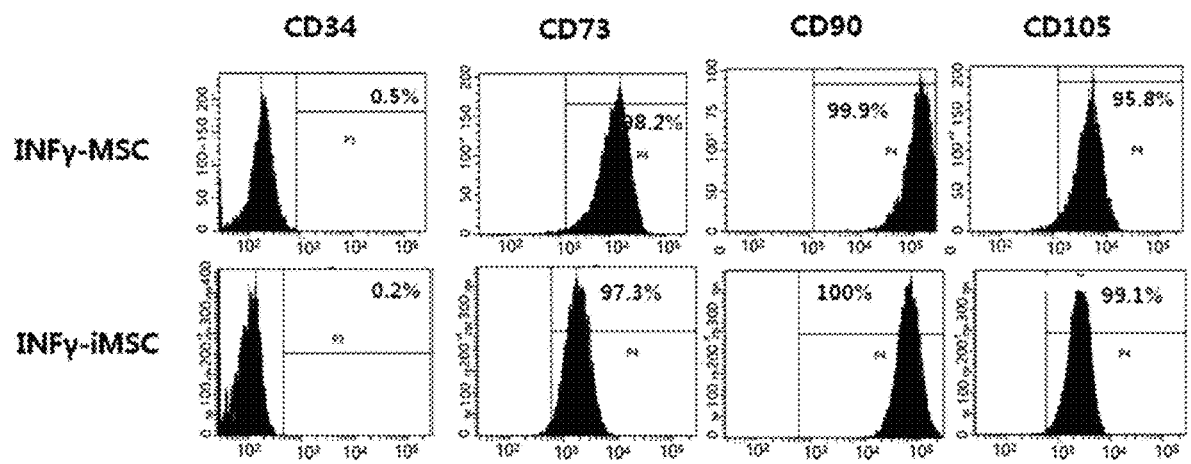
FIG. 2 shows the surface antigen analysis results in iMSC and IFNγ-iMSC.

Flow cytometry was used to investigate whether the interferon-γ-pretreated mesenchymal stem cells showed negative expression for CD34 and positive expression for CD73, CD90, and CD105, which are specific surface antigen markers. The results verified that the induced pluripotent stem cell-derived mesenchymal stem cells had typical characteristics of mesenchymal stem cells (MSCs)—negative expression for CD34 (BD Biosciences, Catalog No.: 348053), positive expression for CD73 (BD Biosciences, Catalog No.: 550257), CD90 (BD Biosciences, Catalog No.: 555596), and CD105 (BD Biosciences, Catalog No.: 560839) (FIG. 2).

Figure 3:
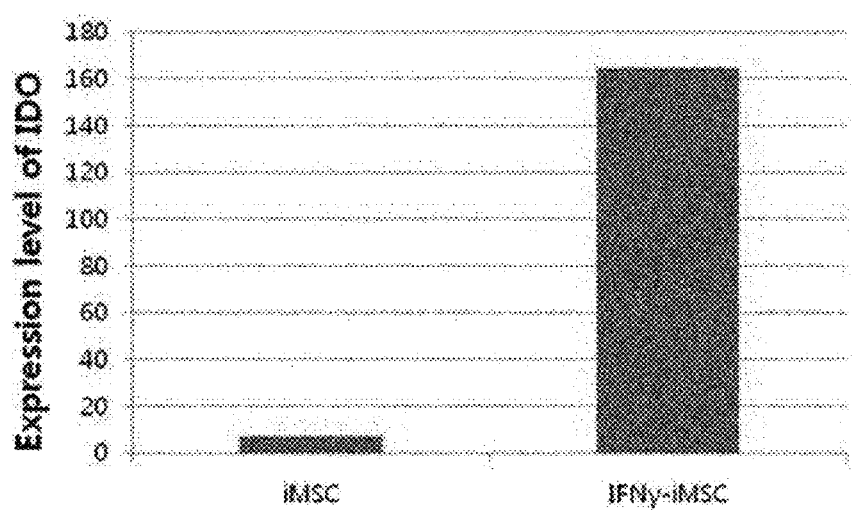
FIG. 3 shows the results of verifying expression levels of IDO in iMSC and IFNγ-iMSC.
Figure 4:
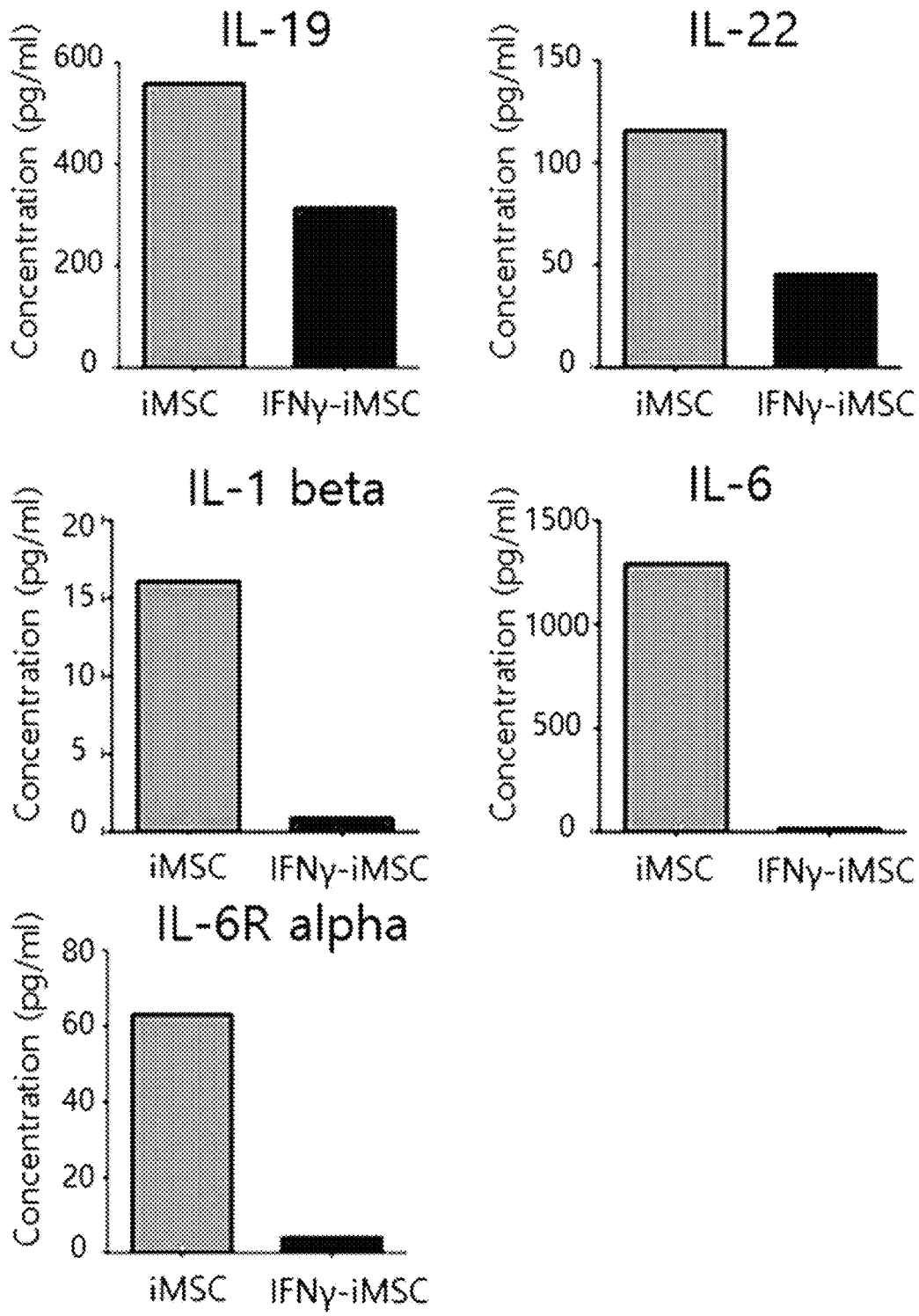
FIG. 4 shows the results of verifying levels of secretion of cytokines in iMSC and IFNγ-iMSC.

In addition, RT-PCR was used to quantify indoleamine 2,3-dioxygenase (IDO) in the induced pluripotent stem cell-derived mesenchymal stem cells (iMSCs) and the interferon-γ-pretreated induced pluripotent stem cell-derived mesenchymal stem cells (IFNγ-iMSCs). The results verified that the expression of IDO was higher in the interferon-γ-pretreated induced pluripotent stem cell-derived mesenchymal stem cells (IFNγ-iMSCs) than the induced pluripotent stem cell-derived mesenchymal stem cells (iMSCs) (FIG. 3).

TABLE 1

Sequences of primers for detection of indoleamine 2,3-dioxygenase (IDO)

| | |
|---|---|
| Forward primer (SEQ ID NO: 1) | 5'-GCCCTTCAAGTGTTTCACCAA-3' |
| Reverse primer (SEQ ID NO: 2) | 5'-GCCTTTCCAGCCAGACAAATAT-3' |

The indoleamine 2,3-dioxygenase is an enzyme that converts tryptophan into kynurenine, and is known to deplete tryptophan in the periphery of cells and inhibits the proliferation of immune cells, thereby suppressing inflammation and immune responses. It can be therefore seen that IFNγ-iMSCs of the present invention with high IDO expression has higher immune response inhibitory activity than iMSC.

In addition, the cultures of the induced pluripotent stem cell-derived mesenchymal stem cells (iMSCs) and the interferon-γ-pretreated induced pluripotent stem cell-derived mesenchymal stem cells (IFNγ-iMSCs) were respectively collected to measure and compare the levels of secretion of inflammation-related cytokine proteins ((IL-1β, IL-19, IL-22, IL-6, and IL-6Rα) therebetween.

It can be seen from the above results that the IFNγ-iMSCs of the present invention are novel mesenchymal stem cells having cytological characteristics (immunological characteristics) distinguished from those of existing iMSCs.

The measurement of inflammation-related cytokines was conducted by Magnetic Luminex® Screening Assay. First, the cultures of MSCs and iMSCs were vortexed and then centrifuged, and the supernatants were ½ diluted with a diluent, thereby preparing respective samples. The samples were incubated with the bead-Ab mixture at room temperature for 2 hours, and after the completion of the reaction, the cytokines were measured by the Luminex instrument (Luminex, Austin, Tex., USA). The respective analytes in the sample reacted with corresponding antibodies attached to particular number beads, respectively and independently, and the detection antibody reacted with 2'(streptavidin-PE) (sandwich assay). For the assay results, the fluorescence level of phycoerythrin (PE) attached to the corresponding bead surface in proportion to the amount of each analyte was measured. In the Luminex instrument, while beads were allowed to flow one by one, the bead number was checked and the PE fluorescence intensity of the bead surface was measured to obtain the reaction result value (MFI) of each analyte. The standard curve was calculated by the best fit method in the calculation software "MasterPlex QT 2010 (MiraiBio, Hitachi, Calif., USA)" from the reaction measurement value (MFI) for each standard concentration, and on the basis of the standard curve, the resultant concentration value of the corresponding sample was calculated by reflecting the dilution factor.

As a result, it can be seen that the interferon-gamma-pretreated induced pluripotent stem cell-derived mesenchymal stem cells (IFNγ-iMSCs) of the present invention are novel mesenchymal stem cells having cytological characteristics (immunological characteristics) distinguished from those of existing induced pluripotent stem cell-derived mesenchymal stem cells (iMSCs) that has not been pretreated with interferon-gamma.

EXAMPLE 2

Isolation and Verification of Exosomes Derived from Induced Pluripotent Stem Cell-Differentiated Mesenchymal Stem Cells Depending on Interferon-Gamma Pretreatment Induced pluripotent stem cell-derived mesenchymal stem cells (iMSCs) and interferon-γ-pretreated induced pluripotent stem cell-derived mesenchymal stem cells (IFNγ-iMSCs) were additionally cultured in culture media supplemented with 10% exosome-depleted FBS. After cell culture for 72 hours, the cultures of the induced pluripotent stem cell-derived mesenchymal stem cells were collected and centrifuged at 300×g for 10 minutes, thereby removing remaining cells and cell debris. The supernatants were filtered using a 0.22-μm filter, and then centrifuged at 10000×g for 70 minutes at 4° C. by using a high-speed centrifuge. The centrifuged supernatants were centrifuged at 100,000×g and 4° C. for 90 minutes using an ultracentrifuge, thereby removing supernatants, and the exosomes remaining in the bottom layer were diluted with phosphate buffered saline (PBS) before use.

Figure 5:
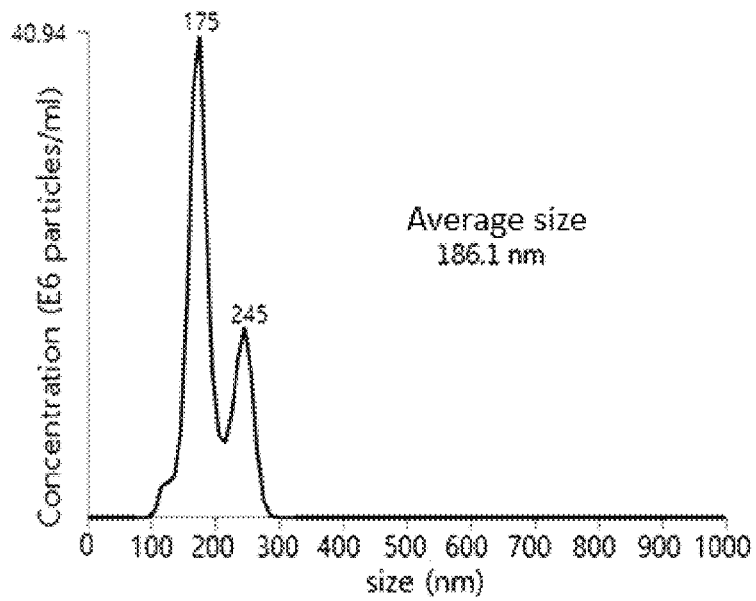
FIG. 5 shows the results of verifying average sizes of exosomes isolated from induced pluripotent stem cell-derived mesenchymal stem cells (iMSC-exo) and exosomes isolated from interferon-gamma-pretreated induced pluripotent stem cell-derived mesenchymal stem cells (IFNγ-iMSC-exo).
Figure 5:
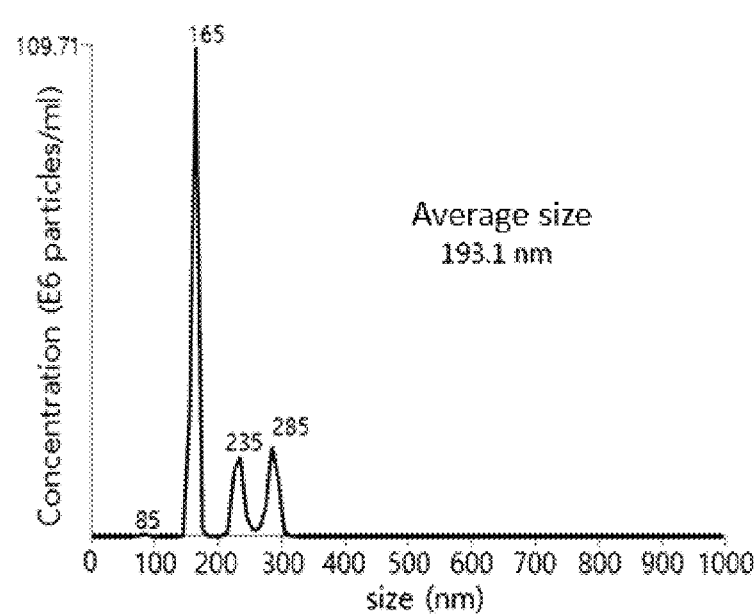
Figure 6:
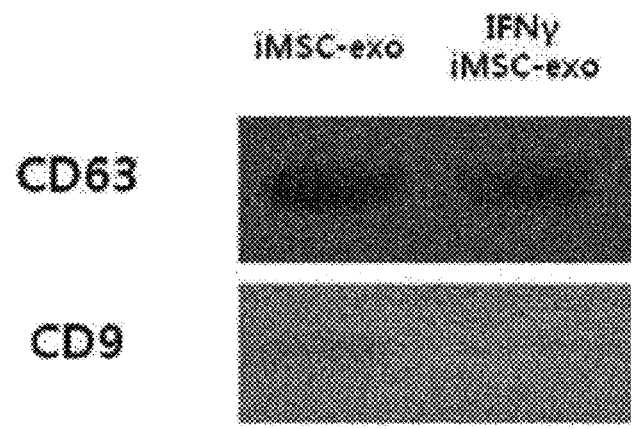
FIG. 6 shows the results of verifying the expression of CD63 and CD9 in iMSC-exo and IFNγ-iMSC-exo.

The exosomes respectively isolated from the cultures of iMSCs and IFNγ-iMSCs were analyzed for the number of exosomes and the size distribution of exosomes by using nanoparticle tracking assay (NanoSight NS300, Malvern) (FIG. 5). The expression of CD9 and CD63, which are exosome-specific surface antigens, was verified by western blotting (FIG. 6).

It can be therefore confirmed that the exosomes respectively derived from iMSCs and the IFNγ-iMSCs of the present invention had the same characteristics as exosomes irrespective of the treatment with or without IFNγ.

EXAMPLE 3

Atopic Disease-Induced Mice Fabrication and Administration

Eight-week-old BALB/c female mice (Orient Bio, South Korea) as experimental animals were purchased and acclimated for one week, and then used in the experiments at 9 weeks of age. For the induction of atopic dermatitis, the backs of the BALB/c mice were shaved to the upper part as much as possible by a shaver. Aspergillus fumigates (Af) extract (40 μg) was applied to the shaved dorsal skin tissue (1×1 cm$^2$) at intervals of 24 hours for 5 days. After 2-week rest period, the extract was repeatedly applied five times at intervals of 24 hours from day 19, to thereby establish atopic dermatitis animal models.

Figure 7:
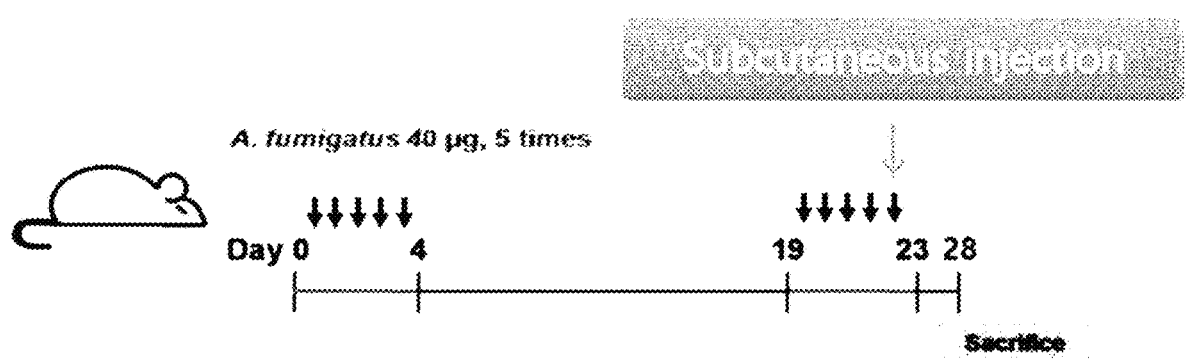
FIG. 7 schematically shows a fabricating procedure of an atopic dermatitis animal model.

After the establishment of atopic dermatitis animal models, the mice were subcutaneously injected with iMSCs, IFNγ-iMSCs, iMSC-exo (exosomes from induced pluripotent stem cell-derived mesenchymal stem cells), and IFNγ-iMSC-exo (exosomes from interferon-γ-pretreated induced pluripotent stem cell-derived mesenchymal stem cells). iMSCs or IFNγ-iMSCs were injected at 2×10$^6$ cells per animal, and iMSC-exo or IFNγ-iMSC-exo were injected at 12 μg per animal. The mice were sacrificed and analyzed on day 5 after the injection (FIG. 7).

EXAMPLE 4

Evaluation on Therapeutic Effect on Atopic Dermatitis by Interferon-Gamma-Pretreated Induced Pluripotent Stem Cell-Derived Mesenchymal Stem Cells (IFNγ-iMSCs) and Exosomes Derived Therefrom (IFNγ-iMSC-exo)

(1) Atopic Symptom Alleviation

Figure 8:
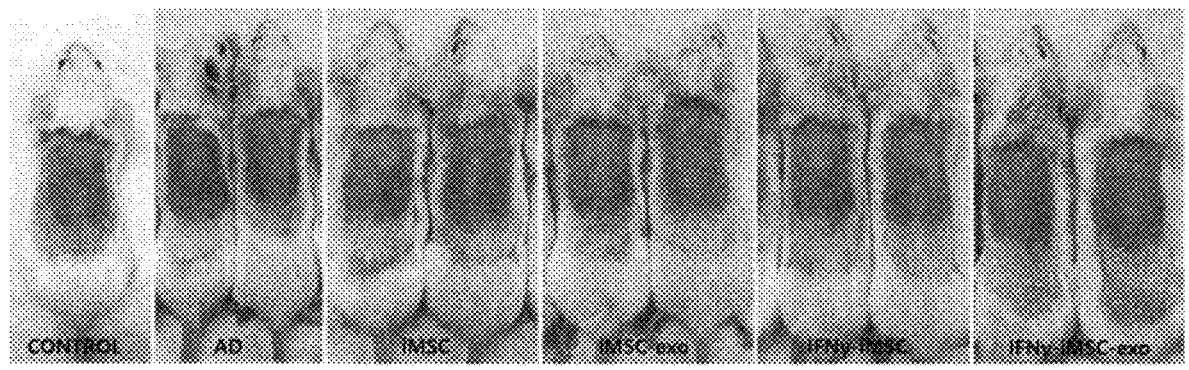
FIG. 8 shows the results of verifying the effects of IFNγ-iMSC and IFNγ-iMSC-exo on atopic lesions of atopic dermatitis animal models.

To investigate the atopy alleviation levels of IFNγ-iMSCs and IFNγ-iMSC-exo, a negative control group without atopic dermatitis (CONTROL, physiological saline treatment), a positive control group with atopic dermatitis (AD, Af treatment), an iMSC treatment group, an IFNγ-iMSC treatment group, an iMSC-exo treatment group, and an IFNγ-iMSC-exo treatment group were observed and compared. As a result, the IFNγ-iMSC treatment group and the IFNγ-iMSC-exo treatment group showed an atopy alleviation effect at similar levels compared with the negative control group (FIG. 8).

(2) Skin Clinical Scores and Transepidermal Water Loss Evaluation

Figure 9:
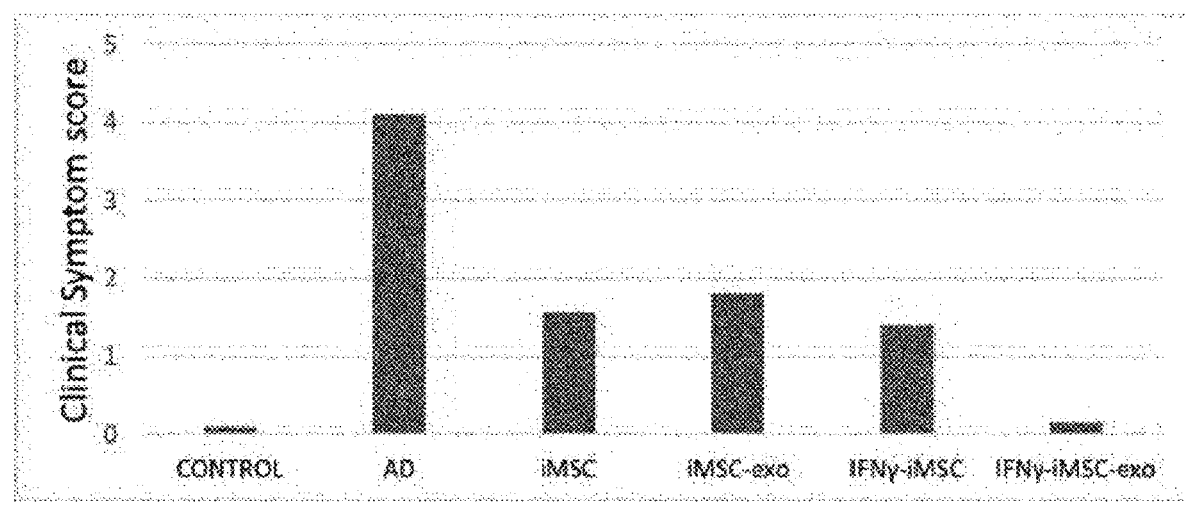
FIG. 9 shows the skin clinical score results by IFNγ-iMSC and IFNγ-iMSC-exo treatment in atopic dermatitis animal models.

Skin clinical scores were set according to five items: dryness, scaling, erosion, excoriation, and bleeding. As for each item, the lesion-free condition was set to 0 points, the mild condition to 1 point, the moderate condition to 2 points, and the severe condition to 3 points. The corresponding points were summarized to calculate a skin clinical score. As a result, the IFNγ-iMSC treatment group and the IFNγ-iMSC-exo treatment group showed more improved skin clinical scores compared with the positive control group (AD), the negative control group (CONTROL), the iMSC treatment group, and the iMSC-exo treatment group. Especially, the IFNγ-iMSC-exo treatment group showed a skin clinical score at the similar level compared with the negative control, indicating an improvement in atopic symptoms (TABLE 2 and FIG. 9).

TABLE 2

Skin clinical scores

| CONTROL | AD | iMSC | iMSC-exo | IFNγ-iMSC | IFNγ-iMSC-exo |
|---|---|---|---|---|---|
| 0.1 | 4.1 | 1.56 | 1.8 | 1.4 | 0.15 |

Figure 10:
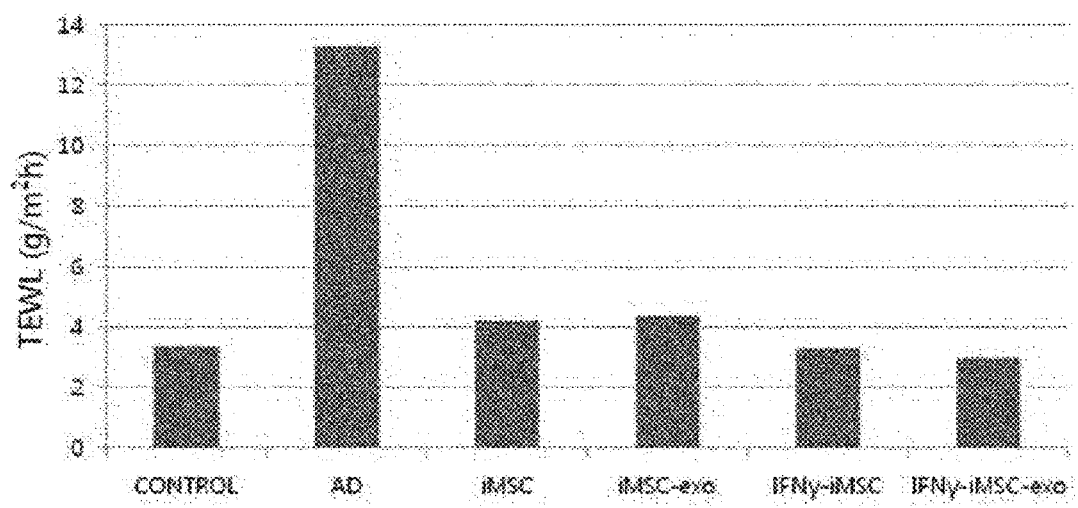
FIG. 10 shows the transepidermal water loss by IFNγ-iMSC and IFNγ-iMSC-exo treatment in atopic dermatitis animal models.

To evaluate skin barrier damage in the same administration groups, the transepidermal water loss (TEWL) was measured using VapometerSWL-3® (Delfin technologies). The results verified that the IFNγ-iMSC treatment group and the IFNγ-iMSC-exo treatment group showed similar levels of transepidermal water loss compared with the negative control group, indicating the improvement in atopic symptoms (Table 3 and FIG. 10).

TABLE 3

Transepidermal water loss (tewl) levels

| CONTROL | AD | iMSC | iMSC-exo | IFNγ-iMSC | IFNγ-iMSC-exo |
|---|---|---|---|---|---|
| 3.4 | 13.3 | 4.2 | 4.4 | 3.3 | 3 |

It can be therefore seen that the IFNγ-iMSCs and IFNγ-iMSC-exo of the present invention alleviate skin clinical symptoms and significantly reduce transepidermal water loss levels, thereby showing excellent effects of alleviating or treating of skin diseases including atopic dermatitis.

(3) Skin Histological Observation

Figure 11:
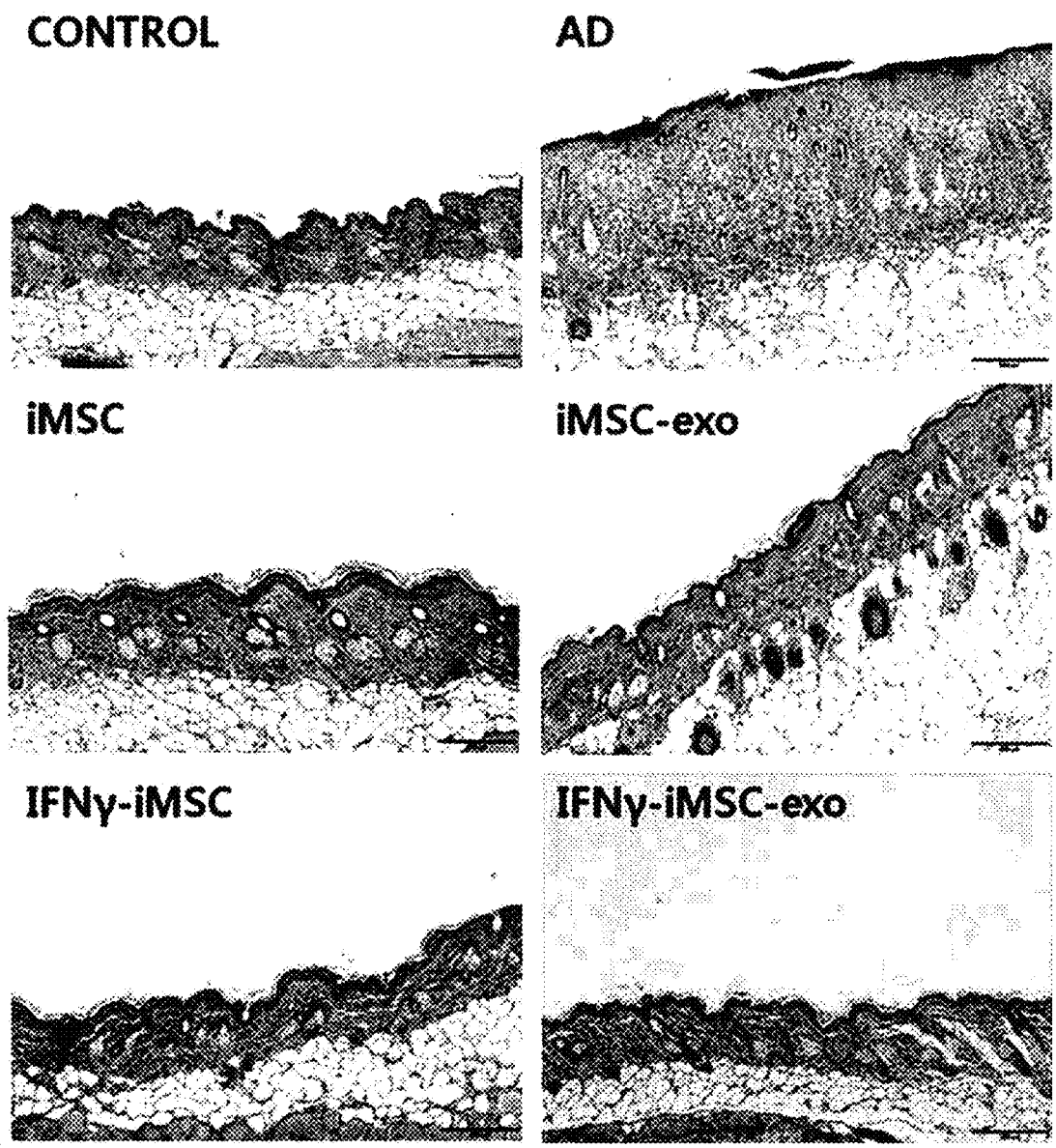
FIG. 11 shows skin histological changes by IFNγ-iMSC and IFNγ-iMSC-exo treatment in atopic dermatitis animal models. Scale bars mean 200 μm.

To investigate the alleviation effect on atopic dermatitis, skin tissues were isolated from the negative control group, the positive control group, the iMSC treatment group, the iMSC-exo treatment group, the IFNγ-iMSC treatment group, and the IFNγ-iMSC-exo treatment group. The isolated skin tissues were fixed with 10% formalin solution, embedded in paraffin, and then cut into sections to 5 μm. To observe skin histological changes and inflammatory cell invasion, skin sections were stained with hematoxylin and eosin and observed under a microscope at 400× magnification. As a result, compared with the positive control group, the IFNγ-iMSC treatment group and the IFNγ-iMSC-exo treatment group showed an amelioration of stratum corneum damage and a reduction in thickness of epidermal and dermal layers (FIG. 11).

It can be therefore seen that the IFNγ-iMSCs and IFNγ-iMSC-exo of the present invention alleviate stratum corneum damage and reduce the thickness of epidermal and dermal layers, thereby showing excellent effects of alleviating or treating skin diseases including atopic dermatitis.

(4) Serum IgE Measurement

Figure 12:
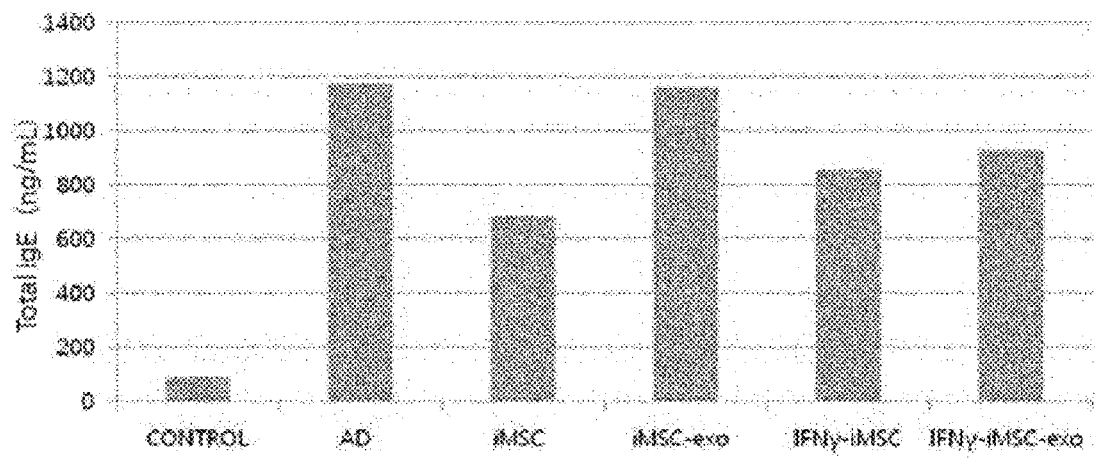
FIG. 12 shows the serum IgE levels by IFNγ-iMSC and IFNγ-iMSC-exo treatment in atopic dermatitis animal models.

In the negative control group, the positive control group, the iMSC treatment group, the iMSC-exo treatment group, the IFNγ-iMSC treatment group, and the IFNγ-iMSC-exo treatment group, the mouse was cut opened its abdomen, and about 0.5-0.7 mL of blood was collected from the postcaval vein after needle insertion. The isolated blood was centrifuged, and then serum was separated. The total IgE levels in the separated serum were measured using an ELISA test kit (eBioscience). As a result, the serum IgE level was reduced in the iMSC treatment group compared with the positive control group, but the serum IgE level was not greatly changed in the iMSC-exo treatment group, and the drop in serum IgE was smaller in the IFNγ-iMSC treatment group and the IFNγ-iMSC-exo treatment group compared with the iMSC treatment group and the iMSC-exo treatment group (FIG. 12).

Based on the above results and clinical symptom improvement effects in the above-described examples, the skin disease alleviating efficacy of the iMSCs, iMSC-exo, IFNγ-iMSCs, or IFNγ-iMSC-exo of the present invention is not mainly medicated by IgE.

(5) Verification on T Cell Immune Response

Figure 13:
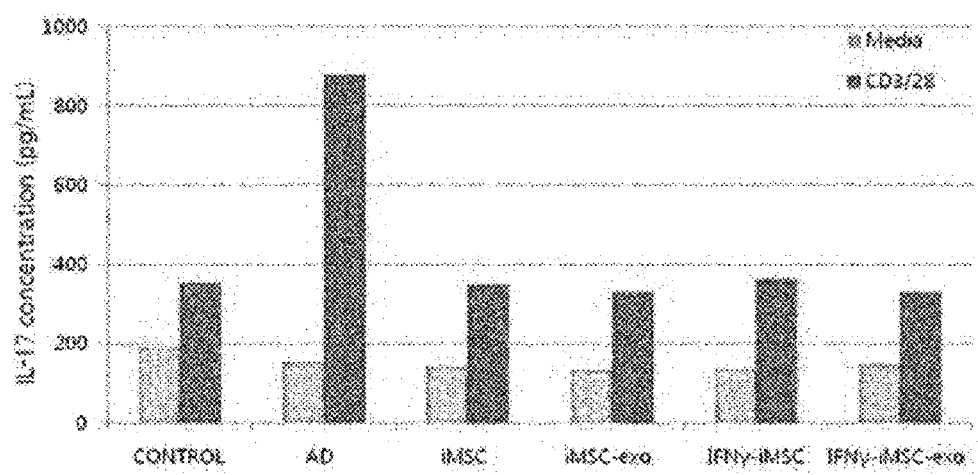
FIG. 13 shows the level of secretion of IL-17a of lymphocytes by IFNγ-iMSC and IFNγ-iMSC-exo treatment in atopic dermatitis animal models.

To investigate T cell immune response by IFNγ-iMSCs and IFNγ-iMSC-exo, lymphocytes were isolated from lymph nodes of the mouse in the negative control group, the positive control group, the iMSC treatment group, the iMSC-exo treatment group, the IFNγ-iMSC treatment group, and the IFNγ-iMSC-exo treatment group. The isolated lymphocytes were stimulated by CD3/CD28 and the cultures were collected, and the cytokine secretion was measured through an ELISA kit (eBioscience). As for the level of IL-17a, which is a main cytokine produced in Th17, the levels of IL-17a in the IFNγ-iMSC treatment group and the IFNγ-iMSC-exo treatment group, compared with the positive control group, were significantly reduced to similar levels to the negative control group (FIG. 13).

Based on the above results and the clinical symptom improvement effects and serum IgE level changes in the above-described examples, the skin disease alleviation efficacy of the IFNγ-iMSCs and IFNγ-iMSC-exo of the present invention was not mainly mediated by IgE, but by inhibition of immune response of T cells, such as IL-17A.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for treating or alleviating a skin disease selected from the group consisting of atopic dermatitis, contact dermatitis, and psoriasis, in a subject in need thereof, comprising:

administering to the subject a composition comprising (i) interferon-gamma-pretreated mesenchymal stem cells or a culture thereof, or (ii) exosomes isolated from interferon-gamma-pretreated mesenchymal stem cells or a culture thereof, wherein the mesenchymal stem cells are induced pluripotent stem cell-derived mesenchymal stem cells (iMSC).

2. The method of claim 1, wherein the subject is a mammal or a human.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Forward primer for detection of human
      indoleamine 2,3-dioxygenase gene

<400> SEQUENCE: 1
gcccttcaag tgtttcacca a     21

-continued

```
<210> SEQ ID NO 2
<211> LENGTH: 22
<212> TYPE: DNA
<213> ORGANISM: Artificial Sequence
<220> FEATURE:
<223> OTHER INFORMATION: Reverse primer for detection of human
      indoleamine 2,3-dioxygenase gene

<400> SEQUENCE: 2
gcctttccag ccagacaaat at                                              22
```